United States Patent [19]

Hoshiyama et al.

[11] 4,225,743
[45] Sep. 30, 1980

[54] DIMERIZATION OF BUTENES CONTAINING ISOBUTENE TO MINIMIZE 2,2,4-TRIMETHYL PENTENES

[75] Inventors: Satoshi Hoshiyama; Shuichi Fukushima; Hiroshi Kobayashi; Hideki Takamatsu, all of Funabashi, Japan

[73] Assignee: Nissan Chemical Industries Limited, Tokyo, Japan

[21] Appl. No.: 969,870

[22] Filed: Dec. 15, 1978

[30] Foreign Application Priority Data

Dec. 29, 1977 [JP] Japan .................................. 52/158862

[51] Int. Cl.$^2$ ............................................... C07C 3/10
[52] U.S. Cl. .................................... 585/512; 585/511; 585/521
[58] Field of Search ........................ 585/511, 512, 521

[56] References Cited

U.S. PATENT DOCUMENTS

| | | | |
|---|---|---|---|
| 3,321,546 | 5/1967 | Roest et al. | 585/512 |
| 3,355,510 | 11/1967 | Cannell et al. | 585/512 |
| 3,592,869 | 7/1971 | Cannell | 585/512 |

Primary Examiner—C. Davis
Attorney, Agent, or Firm—Oblon, Fisher, Spivak, McClelland & Maier

[57] ABSTRACT

In a dimerization of butenes containing isobutene, a formation of 2,2,4-trimethyl pentenes is minimized by using a specific nickel catalyst solution and an organoaluminum catalyst. The specific nickel catalyst is a nickel salt of a fatty acid having 1.5 to 40 wt. % of a free fatty acid and less than 0.1 wt. % of water.

The $C_8$ olefins having less 2,2,4-trimethyl pentenes obtained by the dimerization are quite important to produce excellent plasticizer.

10 Claims, No Drawings

DIMERIZATION OF BUTENES CONTAINING ISOBUTENE TO MINIMIZE 2,2,4-TRIMETHYL PENTENES

BACKGROUND OF THE INVENTION

The present invention relates to a dimerization of butenes containing isobutene to minimize a formation of 2,2,4-trimethyl pentenes.

Heretofore, it has been known to obtain dimers by a dimerization of n-butenes using each of various catalyst systems comprising a nickel salt and an aluminum compound.

However, it has been considered that if isobutene is included in the starting material of n-butene, tertiary carbon in isobutene is converted into carbonium ion by an aluminum compound whereby higher oligomers are produced. Even though the reaction is stopped in the stage of the dimerization by selecting the reaction conditions, the resulting $C_8$ olefins include 2,2,4-trimethyl pentenes having quaternary carbon which cause inferior properties.

Accordingly, it has been considered to be necessary to remove isobutene in the dimerization of butenes or to separate a by-product formed from isobutene as high boiling point product after the dimerization of butenes.

The inventors have studied to various processes for a dimerization of isobutene with a dimerization of n-butene and have succeeded in reducing a formation of 2,2,4-trimethyl pentenes.

SUMMARY OF THE INVENTION

It is an object of the present invention to provide a dimerization of butenes containing isobutene to minimize a formation of 2,2,4-trimethyl pentenes by forming 2-methyl heptenes and 2,4-dimethyl hexenes.

The foregoing and other objects of the present invention have been attained by a dimerization of a $C_4$ fraction containing 5 to 55 wt.% of isobutene with a catalyst system of a nickel salt of a fatty acid and 1.5 to 40 wt.% of a free fatty acid which has less than 0.1 wt.% of water content and an organoaluminum halide.

DETAILED DESCRIPTION OF THE PREFERRED EMBODIMENTS

The nickel salts used in the present invention are nickel (II) salts of fatty acids which can be obtained by reacting a nickel salt with a fatty acid.

Typical fatty acids include heptylic acid, octylic acid, nonanoic acid, decanoic acid, dodecanoic acid, tridecanoic acid and octadecanoic acid. The fatty acids can have straight skeletal form or have high branched degree. The fatty acids can be also naphthenic acid.

It is especially preferable to use a fatty acid having carbon atoms of 11 to 18.

It is preferable to use the nickel salt of fatty acid with a free fatty acid at a ratio of the free fatty acid to the nickel salt of 0.02 to 0.6 by weight.

Typical nickel salts of fatty acid include natural fatty acid derivatives such as $(n-C_{11}H_{23}COO)_2Ni$, $(n-C_{17}H_{35}COO)_2Ni$, $(n-C_{15}H_{31}COO)_2Ni$ (percent straight chain 100%) and synthetic fatty acid derivatives having a percent straight chain of 0 to 65% and the formula
$(C_{10}H_{21}COO)_2Ni$;
$(C_{11}H_{22}COO)_2Ni$;
$(C_{12}H_{25}COO)_2Ni$;
$(C_{11}H_{23}COO)(C_{12}H_{25}COO)Ni$;
$(C_{17}H_{35}COO)_2Ni$;
$(C_{14}H_{29}COO)_2Ni$; and
$(C_{13}H_{27}COO)(C_{14}H_{29}COO)Ni$.

These nickel salts of fatty acid can be obtained by the conventional methods, for example, by reacting an alkali metal salt of the fatty acid with an aqueous solution of a nickel salt such as nickel chloride, nickel nitrate and nickel sulfate preferably nickel chloride in a form of an aqueous solution at 70° to 80° C. The resulting nickel salt of fatty acid is separated as a precipitate.

The synthetic fatty acids can be obtained by converting n-olefin and branched olefin, by an oxo reaction, to the corresponding alcohols having 0 to 65% of straight chain alcohol component and 35 to 100% of branched chain alcohol component such as $C_{11}H_{23}OH$, $C_{12}H_{25}OH$, $C_{13}H_{27}OH$, $C_{14}H_{29}OH$ and $C_{15}H_{31}OH$ and mixtures thereof, and then, oxidizing the alcohol to the corresponding carboxylic acid by the conventional method.

The resulting nickel salt of fatty acid is solid or high viscosity liquid at room temperature and it is dissolved in suitable organic solvent to use it as the catalyst.

Suitable solvents include $C_5$-$C_7$ saturated hydrocarbons or aliphatic monoolefins having 6 or more carbon atoms preferably $C_8$ aliphatic monoolefin. It is also possible to use the other solvents such as aromatic hydrocarbons which do not interrupt the dimerization of butenes and can be easily separated from the reaction product.

However, the solubility of the nickel salt of fatty acid in the organic solvents at room temperature is different and sometimes, the nickel salt can be dissolved with a free fatty acid.

When the nickel salt of fatty acid is not dissolved in the dimerization, non-uniform distribution of the catalyst and the deterioration of reaction are caused.

Accordingly, it is important to consider solubilities of the nickel salt of fatty acid and a free fatty acid.

Certain examples for improving the solubility of the nickel salt of fatty acid in n-heptane by adding a free fatty acid are shown.

| Type of nickel salt of fatty acid | Amount of free fatty acid for dissolving nickel salt in n-heptane (to 100 wt. parts of Ni salt) (wt. part) |
|---|---|
| $(n-C_{11}H_{23}COO)_2Ni$ | more than 10 |
| $(n-C_{13}H_{27}COO)_2Ni$ | more than 15 |
| $(n-C_{15}H_{31}COO)_2Ni$ | more than 25 |
| $(C_{10}H_{21}COO)_2Ni$ | more than 4 |
| $(C_{11}H_{23}COO)_2Ni$ | |
| $(C_{12}H_{25}COO)_2Ni$ | |
| $(C_{11}H_{23}COO)(C_{12}H_{25}COO)Ni$ | more than 8 |
| $(C_{13}H_{27}COO)_2Ni$ | |
| $(C_{14}H_{19}COO)_2Ni$ | more than 10 |
| $(C_{13}H_{27}COO)(C_{14}H_{29}COO)Ni$ | |

In the present invention, the catalytic activity and the selectivity of the nickel catalyst in the reaction system can be further improved by incorporating a free fatty acid in the nickel salt of fatty acid as the catalyst for the dimerization of butenes.

The amount of a free fatty acid is in a range of 1.5 to 40 wt. parts to 100 wt. parts of the nickel salt of fatty acid.

It is not preferable to add more than 40 wt. parts of a free fatty acid since no additional effect is given but it adversely affects to the alkylaluminum halide.

The nickel salt of fatty acid with a free acid in a form of an organic solvent solution which is called as a nickel catalyst solution is used for the dimerization.

The organoaluminum halides used in the present invention have the formula $$R_nAl_2X_{6-n}$$

wherein R represents an alkyl group ($C_1$ to $C_8$); X represents a halogen atom and n is 2 to 6 especially 2 or 3.

The organoaluminum halides are well known in the arts.

Suitable organoaluminum halides include ethylaluminum dichloride, ethylaluminum sesquichloride, diethylaluminum chloride and other alkylaluminum halides such as propyl- or isobutylaluminum halides.

In order to obtain the object reaction product, it is preferable to use ethylaluminum dichloride or ethylaluminum sesquichloride.

It is important to reduce a water content in the nickel catalyst solution. The nickel salt of fatty acid is dissolved in heptane or toluene and heptane or toluene is refluxed to remove water so as to give less than 0.1 wt.% to the nickel salt of fatty acid and then, the product is diluted with anhydrous heptane or toluene.

The amount of the solvent can be selected as desired such as 200 to 1200 cc preferably 600 to 1000 cc per 1 g as Ni. The solvent used for diluting the dehydrated nickel salt of fatty acid can be anhydrous aliphatic, alicyclic or aromatic hydrocarbons having a boiling point of lower than 100° C. such as n-hexane, 2-methylpentane, n-pentane, cyclohexane and benzene.

On the other hand, the alkylaluminum chloride can be diluted with suitable solvent, for example, the amount of the solvent can be selected as desired such as 20 to 100 cc preferably 40 to 80 cc per 1 g as Al.

The catalyst solutions are added to butenes for the dimerization system in a reactor which is preferably an autoclave.

In the dimerization, the alkylaluminum halide is added at a ratio of 0.1 to 1.0 wt.% preferably 0.12 to 0.3 wt.% especially 0.16 to 0.24 wt.% to butenes and the nickel salt of fatty acid is added at a molar ratio of Al to Ni of 10:1 to 50:1 preferably 10:1 to 18:1.

The reaction temperature is depending upon the kind of the nickel salt of fatty acid.

For example, when carbon atoms of the fatty acid is, $C_{12}$, $C_{14}$ and $C_{16}$, suitable reaction temperature is respectively 52° C., 60° C. and 72° C.

In usual, when the carbon atoms of fatty acid is the same, the reaction temperature is higher in the case of straight chain in comparison with branched chain since the melting point of the branched chain one is lower than that of the straight chain one. The reaction temperature is usually in a range of 45° to 80° C. preferably higher than 45° C. and the pressure is preferably in a range of 5 to 12 kg/cm² G which is usually caused by spontaneous pressure. The dimerization is carried out in a homogeneous liquid system under thoroughly stirred.

In the dimerization of $C_4$ fraction containing isobutene, it is preferable to add suitable amount of the nickel catalyst solution to the $C_4$ fraction and then, to add suitable amount of the aluminum catalyst solution.

The $C_4$ fraction as the starting material usually purified to contain less than 5 ppm of dienes and acetylenes and less than 30 ppm of oxygen-containing compounds.

In particular purification, a selective hydrogenation is applied for the former purpose and a water washing is applied for the latter purpose.

Moreover, $C_4$ fraction is dried to be less than 5 ppm of water content.

The $C_4$ fraction usually contains 5 to 55% of isobutene and the other components such as n-butene and butanes.

The dimerization can be carried out by a batch system using a closed reactor; a semi-batch system charging intermittently the $C_4$ fraction and the catalyst solutions and a continuous system feeding continuously the $C_4$ fraction and the catalyst.

The octene fraction can be obtained in high yield such as more than 90 wt.% of total of octenes, monomethylheptenes and dimethyl hexenes.

The reaction mixture obtained in the dimerization is distilled to separate $C_8$ fraction. The $C_8$ fraction is useful as a solvent, and a starting material for nonanol. The nonanol is produced by the conventional oxo reaction and it is useful as the alcohol for a plasticizer.

In accordance with the process of the present invention, the formation of dimers having quaternary carbon especially 2,2,4-trimethyl pentenes can be minimized to be less than 6 wt.% especially 3 wt.%.

When olefins having quaternary carbon especially 2,2,4-trimethyl pentenes are incorporated in the dimer of butenes, a plasticizer produced by using the dimer of butenes has inferior cold resistance and plasticizing property.

In accordance with the present invention, it is succeeded to dimerize isobutylene with n-butylene to form 2-methyl heptenes and 2,4-dimethyl hexenes.

The kinds of dimers of butenes are as follows:

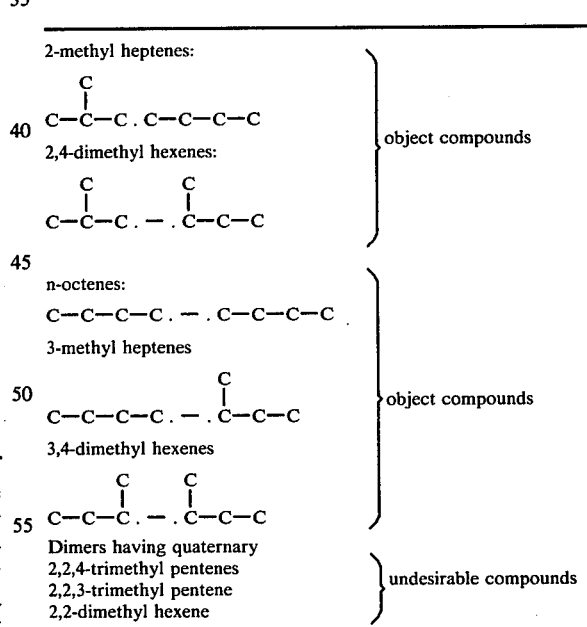

It is well known that B-B fraction obtained by a thermal cracking of naphtha, contain butadiene, isobutene, n-butene, n-butane and isobutane, etc. Butadiene is separated by an extraction and is used for various syntheses. The remained spent B-B fraction contain isobutene, n-butene, and n-butane, etc. is mostly used as a fuel of LPG and is partially used as a starting material for other compounds or gasoline.

The B-B fraction obtained by a thermal cracking of heavy oil is mostly used as fuel.

It is not easy to separate isobutene from n-butene and accordingly, it is important to use a mixture of isobutene and n-butene as a starting material for syntheses. In the conventional process, when isobutene is incorporated, relatively large amount of 2,2,4-trimethyl pentenes are formed. However, in accordance with the process of the present invention, a formation of dimers having quaternary carbon especially 2,2,4-trimethyl pentenes can be minimized. When the dimer of butenes incorporating 2,2,4-trimethyl pentenes is used for producing a plasticizer by converting the dimer of olefin to the corresponding aldehyde by the conventional oxo reaction with a cobalt carbonyl catalyst and a mixed gas of hydrogen and carbon monoxide (1.0 to 1.5 vol. ratio of $H_2/CO$) under a pressure of 140 to 200 kg/cm$^2$ G at 130° to 180° C. and hydrogenizing the aldehyde to obtain the corresponding alcohol and esterifying the alcohol with phthalic anhydride to obtain $C_9$ alcohol phthalate.

When 2,2,4-trimethyl pentenes are incorporated at a relatively high ratio in the dimer of butenes, the resulting $C_9$ alcohol phthalate has inferior properties especially on plasticization effect and cold resistance.

When the dimer of butenes obtained by the process of the present invention is used, the $C_9$ alcohol phthalate has excellent characteristics as the plasticizer especially on cold resistance, heat resistance, plasticization effect and volume resistivity which are superior to those of dioctyl phthalate (DOP) or dinonyl phthalate (DNP). (DNP is produced by using 2,4,4-trimethyl pentene.)

EXAMPLE 1

Nickel octylate (Ni content of 10.1 wt.%) having a water content of 2.5 wt.% and a free fatty acid content of 37.1 wt.% was prepared.

Then, 10 g of the nickel octylate was dissolved in 80 cc of n-heptane and the solution was heated at 100° C. under refluxing for 3 hours to remove water and then, n-heptane was distilled off to reduce a water content of nickel octylate to 0.06 wt.%.

A nickel catalyst solution was prepared by dissolving 1 g of the dehydrated nickel octylate in 80 cc of n-heptane.

On the other hand, as organoaluminum chloride, 7.3 g of ethylaluminum dichloride was dehydrated and dissolved in 100 cc of n-heptane to prepare and aluminum catalyst solution.

The following dimerization was carried out by using the nickel catalyst solution and the aluminum catalyst solution.

As the starting material of $C_4$ fraction, a sample was prepared by mixing 72 wt.% of n-butene-2, 18 wt.% of isobutene and 20 wt.% of n-butane. The $C_4$ fraction sample was dried with molecular seive 4 A and 200 cc of the $C_4$ fraction sample was charged in a 300 cc glass autoclave equipped with a magnetic stirrer which was kept in a water bath at 30° C.

In the autoclave, 6.4 cc of the nickel catalyst solution was charged under pressure with thoroughly stirring and then 4 cc of the aluminum catalyst solution was charged under pressure. The temperature in the water bath was raised to 40° C. and the reaction was carried out for 5 hours under pressurizing to 4.5 to 5.0 kg/cm$^2$ G by feeding dry nitrogen.

After the reaction, the autoclave was cooled to reduce the pressure to the atmospheric pressure and the reaction mixture was discharged and treated with 30 cc of 5% aqueous solution of sulfuric acid to decompose the catalysts and the reaction mixture was washed with water, and then, it was distilled under the atmospheric pressure to obtain 68.5 g of a distillate at a top temperature of 115° C. to 125° C. and 20.6 g of a bottom residue.

The distillate was hydrogenized with Pd catalyst and the product was analyzed by a gas chromatography equipped with Golay column. The components shown in Table 2 were found.

As the reference, in accordance with the similar process except preparing a nickel catalyst solution without dehydrating nickel octylate, the dimerization was carried out. As the result, only 40.4 g of octenes were obtained and 36.5 g of the bottom residue was obtained.

EXAMPLE 2

In accordance with the process of Example 1, nickel decanoate (Ni content of 10.7 wt.%) having a water content of 1.6 wt.% and a free aliphatic acid of 31.4 wt.% was prepared and water was removed to be a water content of 0.05 wt.%, and a nickel catalyst solution was prepared by using nickel decanoate to use it in the dimerization. The aluminum catalyst solution of Example 1 was used.

As the starting material of $C_4$ fraction, a sample for the dimerization was prepared by mixing 52 wt.% of n-butene-2, 26 wt.% of isobutene and 22 wt.% of n-butane.

In accordance with the process of Example 1, except using the sample and the catalysts, the dimerization was carried out in the same condition to obtain 50.5 g of octenes and 16.0 g of the bottom residue.

In accordance with the process of Example 1, the octenes were hydrogenized and analyzed. The results are shown in Table 2.

EXAMPLE 3

In accordance with the process of Example 1 except using the nickel catalyst solution and the aluminum catalyst solution of Example 2 and the starting material of $C_4$ fraction prepared by mixing 45 wt.% of n-butene-2, 36 wt.% of isobutene and 19 wt.% of n-butane, the dimerization was carried out.

The product was 53.7 g of octenes and 20.6 g of a bottom residue.

In accordance with the process of Example 1, the octenes were hydrogenized and analyzed. The results are shown in Table 2.

TABLE 2

| $C_8$ Component (wt. %) | Example 1 | Example 2 | Example 3 |
|---|---|---|---|
| octenes: C—C—C—C—C—C—C—C | 7.3 | 6.8 | 5.6 |
| 3-methyl heptenes: C—C—C(C)—C—C—C—C | 45.9 | 43.5 | 39.7 |
| 3,4-dimethyl hexanes: C—C—C(C)—C(C)—C—C | 36.9 | 30.1 | 23.8 |
| 2-methyl heptenes: C—C(C)—C—C—C—C—C | 1.9 | 3.7 | 6.4 |
| 2,4-dimethyl hexenes: C—C(C)—C—C(C)—C—C | 6.9 | 12.7 | 19.5 |
| Others | 1.1 | 3.2 | 5.0 |

TABLE 2-continued

| $C_8$ Component (wt. %) | Example 1 | Example 2 | Example 3 |
|---|---|---|---|
| Total | 100.0 | 100.0 | 100.0 | quantitively $C_8$ monoolefins as dimers, $C_{12}$ monoolefins as trimers and higher oligomers.

The reaction conditions and results are shown in Table 3.

TABLE 3

| | Example | | | | | | | | | |
|---|---|---|---|---|---|---|---|---|---|---|
| | 4 | 5 | 6 | 7 | 8 | 9 | 10 | 11 | 12 | 13 |
| Starting material (wt. %) | | | | | | | | | | |
| n-butane | 20 | 20 | 20 | 20 | 20 | 20 | 20 | 20 | 16.2 | 14.9 |
| isobutene | 18 | 18 | 18 | 18 | 18 | 18 | 18 | 18 | 35.1 | 46.5 |
| n-butene | 72 | 72 | 72 | 72 | 72 | 72 | 72 | 72 | 48.7 | 38.6 |
| $R_mAl_2X_{6-m}$ | | | | | | | | | | |
| $EtAlCl_2$ | 0 | 0 | 0 | 0 | 0 | 0 | 0 | 0 | | 0 |
| $Et_3Al_2Cl_3$ | | | | | | | | | | |
| Ratio to starting material (wt. %) | 0.24 | 0.24 | 0.24 | 0.24 | 0.24 | 0.24 | 0.24 | 0.24 | 0.20 | 0.24 |
| Ni catalyst | | | | | | | | | | |
| fatty acid for Ni salt: | | | | | | | | | | |
| n-$C_{12}$ acid | 0 | 0 | 0 | | | | | | | |
| n-$C_{14}$ acid | | | 0 | | | | | | | |
| n-$C_{16}$ acid | | | | 0 | | | | | | |
| n-$C_{11}$ acid | | | | | 0 | | | | | |
| mixture $C_{12}$ and $C_{13}$ acid | | | | | | | 0 | | 0 | 0 |
| mixture $C_{14}$ and $C_{15}$ acid | | | | | | | | 0 | | |
| Ni catalyst | | | | | | | | | | |
| Ratio of free fatty acid (wt. %) | 13.1 | 13.1 | 13.1 | 20.5 | 26.2 | 10.7 | 11.5 | 15.0 | 11.5 | 11.5 |
| Molar ratio of Al/Ni | 15 | 15 | 15 | 15 | 15 | 15 | 15 | 15 | 14 | 16 |
| Reaction | | | | | | | | | | |
| Temperature (°C.) | 52 | 40 | 60 | 61 | 71 | 44 | 52 | 62 | 52 | 52 |
| Time (hr.) | 5 | 7 | 5 | 5 | 5 | 5 | 5 | 5 | 5 | 7 |
| Result of Reaction | | | | | | | | | | |
| Conversion (%) | | | | | | | | | | |
| isolutene | 92 | 85 | 98 | 94 | 93 | 89 | 96 | 94 | 97 | 98 |
| n-butene | 78 | 55 | 61 | 80 | 81 | 78 | 80 | 77 | 68 | 59 |
| Components in product (%) | | | | | | | | | | |
| $C_8$ | 81 | 76 | 70 | 78 | 78 | 82 | 83 | 76 | 58 | 48 |
| $C_{12}$ | 9 | 10 | 12 | 11 | 10 | 11 | 8 | 12 | 11 | 12 |
| $C_{16}$ and higher | 10 | 13 | 18 | 11 | 12 | 7 | 9 | 12 | 31 | 40 |

EXAMPLES 4–13

Each of sodium salts of various natural or synthetic fatty acid (1.1 mole) was dissolved in 1 liter of water and the solution was thoroughly stirred at 75° C. and an aqueous solution of 0.5 mole of nickel chloride ($NiCl_2.6-H_2O$) in 100 cc of water was added dropwise during 15 minutes, to form a precipitate. It was cooled and a green precipitate was filtered and recrystallized from a mixed xylene and dried completely at relatively low temperature. The resulting nickel salts of fatty acids were respectively used in the following dimerizations.

The dimerization was carried out in a 500 cc glass autoclave equipped with a magnetic stirrer.

In the autoclave, 250 cc of each starting material of $C_4$ fraction containing isobutene, n-butene and butanes shown in Table 3 was charged.

A solution of each nickel salt of fatty acid (Ni content of 0.1 to 0.2 g) in 80 ml of heptane was added at a ratio shown in Table 3. The autoclave was kept in a water bath to maintain a specific reaction temperature and a solution of alkylaluminum chloride in n-heptane was further added to perform each dimerization.

After 5 to 7 hours, 5% aqueous solution of sulfuric acid was added to the reaction mixture under pressure to decompose the catalyst and the unreacted isolutene and n-butene in the liquid phase were analyzed by a gas chromatography to measure each conversion.

The unreacted and inert $C_4$ fraction were distilled off. The liquid components were analyzed by a gas chromatography equipped with a precut device to measure In Examples 11, 12 and 13, $C_8$ fractions ($C_8$ components) included the components shown in Table 4.

TABLE 4

| $C_8$ Component (wt. %) | Example 11 | Example 12 | Example 13 |
|---|---|---|---|
| octenes: C—C—C—C—C—C—C—C | 6.9 | 7.5 | 6.0 |
| 3-methyl heptenes: $\begin{array}{c} C \\ | \\ C-C-C-C-C-C-C \end{array}$ | 48.5 | 52.0 | 43.3 |
| 3,4-dimethyl hexanes: $\begin{array}{cc} C & C \\ | & | \\ C-C-C-C-C-C \end{array}$ | 25.5 | 25.3 | 23.2 |
| 2-methyl heptenes: $\begin{array}{c} C \\ | \\ C-C-C-C-C-C-C \end{array}$ | 3.7 | 3.0 | 4.9 |
| 2,4-dimethyl hexenes: $\begin{array}{cc} C & C \\ | & | \\ C-C-C-C-C-C \end{array}$ | 12.2 | 8.4 | 17.5 |
| Others | 3.2 | 3.8 | 5.1 |
| Total | 100.0 | 100.0 | 100.0 |

What is claimed is:

1. In a dimerization of a $C_4$ fraction containing 5 to 55% of isobutene and a main component of n-butene to minimize the formation of 2,2,4-trimethyl pentenes, the improvement comprising carrying out the dimerization of butenes in the presence of a catalyst system of a nickel salt of fatty acid and 1.5 to 40 wt.% of a free fatty acid having less than 0.1 wt.% of a water content and an organoaluminum halide.

2. A dimerization according to claim 1 wherein the nickel salt of fatty acid and the free fatty acid are dissolved in an organic solvent and water is removed from the solution to less than 0.1 wt.%.

3. A dimerization according to claim 1 wherein the organoaluminum halide is dissolved in an organic solvent and the solution is added to butenes after adding a solution of the nickel salt of fatty acid.

4. A dimerization according to claim 1 wherein the nickel salt of fatty acid is prepared by using a fatty acid having carbon atoms of 11 to 16.

5. A dimerization according to claim 1 wherein the free fatty acid is added at a ratio of 0.02 to 0.6 by weight to the nickel salt of fatty acid.

6. A dimerization according to claim 1 wherein the free fatty acid is the same with the fatty acid for the nickel salt.

7. A dimerization according to claim 1 wherein the organoaluminum halide having the formula $$R_nAl_2X_{6-n}$$

wherein R represents an alkyl group; X represent a halogen atom; n is 2 to 6.

8. A dimerization according to claim 1 wherein a molar ratio of Al to Ni is 10:1 to 50:1 as the ratio of the organoaluminum halide to the nickel salt of fatty acid.

9. A dimerization according to claim 1 wherein the dimerization is carried out in an autoclave under a pressure of 5 to 12 kg/cm$^2$ G at 45° to 70° C. in a batch system or in a continuous system.

10. A dimerization according to claim 7, wherein n is 2 or 3.

* * * * *